United States Patent
Hara et al.

(10) Patent No.: US 6,545,136 B1
(45) Date of Patent: Apr. 8, 2003

(54) PROCESS FOR PRODUCING DESULFATED POLYSACCHARIDE, AND DESULFATED HEPARIN

(75) Inventors: Saburo Hara, Osaka (JP); Keiichi Yoshida, Tokyo (JP); Masayuki Ishihara, Tokyo (JP)

(73) Assignee: Seikagaku Corporation (JP)

( * ) Notice: Subject to any disclaimer, the term of this patent is extended or adjusted under 35 U.S.C. 154(b) by 0 days.

(21) Appl. No.: 09/604,582

(22) Filed: Jun. 27, 2000

Related U.S. Application Data

(60) Division of application No. 08/765,392, filed on Dec. 27, 1996, now Pat. No. 6,140,481, and a continuation-in-part of application No. PCT/JP95/01321, filed on Jul. 3, 1995.

(30) Foreign Application Priority Data

Jul. 1, 1994 (JP) .............................. 6-151258

(51) Int. Cl.[7] .............................................. C08B 37/10
(52) U.S. Cl. ............................ 536/21; 514/56; 514/925
(58) Field of Search ........................... 536/21; 514/56, 514/925

(56) References Cited

U.S. PATENT DOCUMENTS 5,583,121 A * 12/1996 Chaudry et al.

OTHER PUBLICATIONS

Rice et al, "Study of Structurally Defined Oligosaccharide Substrates of Heparin and Heparan Monosulfate Lyases", Carbohydrate Research, 190 (1989) pp. 219–233.*

* cited by examiner

*Primary Examiner*—James O. Wilson
*Assistant Examiner*—Everett White
(74) *Attorney, Agent, or Firm*—Bierman, Muserlian and Lucas

(57) ABSTRACT

This invention relates to a process for producing a desulfated polysaccharide, which comprises reacting a sulfated polysaccharide having a saccharide in which a primary hydroxyl group is sulfated, as a constituent sugar, with a silylating agent represented by the following formula (I)

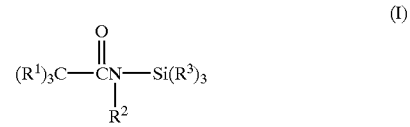

wherein $R^1$s are the same or different and each represent a hydrogen atom or a halogen atom, $R^2$ represents a lower alkyl group, and $R^3$s are the same or different and each represent a lower alkyl group, an aryl group or a halogen atom, and a desulfated heparin obtained by this production process.

4 Claims, 2 Drawing Sheets

|  | $R^1$ | $R^2$ | $R^3$ |
|---|---|---|---|
| ΔDiHS-0S | H | Ac | H |
| ΔDiHS-6S | $SO_3^-$ | Ac | H |
| ΔDiHS-NS | H | $SO_3^-$ | H |
| ΔDiHS-US | H | Ac | $SO_3^-$ |
| ΔDiHS-di(6,N)S | $SO_3^-$ | $SO_3^-$ | H |
| ΔDiHS-di(U,N)S | H | $SO_3^-$ | $SO_3^-$ |
| ΔDiHS-di(U,6)S | $SO_3^-$ | Ac | $SO_3^-$ |
| ΔDiHS-tri(U,6,N)S | $SO_3^-$ | $SO_3^-$ | $SO_3^-$ |

|  | $R^1$ | $R^2$ | $R^3$ |
|---|---|---|---|
| ΔDiHS-0S | H | Ac | H |
| ΔDiHS-6S | $SO_3^-$ | Ac | H |
| ΔDiHS-NS | H | $SO_3^-$ | H |
| ΔDiHS-US | H | Ac | $SO_3^-$ |
| ΔDiHS-di(6,N)S | $SO_3^-$ | $SO_3^-$ | H |
| ΔDiHS-di(U,N)S | H | $SO_3^-$ | $SO_3^-$ |
| ΔDiHS-di(U,6)S | $SO_3^-$ | Ac | $SO_3^-$ |
| ΔDiHS-tri(U,6,N)S | $SO_3^-$ | $SO_3^-$ | $SO_3^-$ |

PROCESS FOR PRODUCING DESULFATED POLYSACCHARIDE, AND DESULFATED HEPARIN

This application is a division of U.S. patent application Ser. No. 08/765,392 filed Dec. 27, 1996, now U.S. Pat. No. 6,140,481, which is a 371 of PCT/JP95/01321 filed Jul. 3, 1995.

TECHNICAL FIELD

This invention relates to a process for producing a desulfated polysaccharide, in which a sulfate group(s) bonded to a primary hydroxyl group(s) of a sulfated polysaccharide is/are selectively desulfated, and a desulfated heparin obtained by this production process.

BACKGROUND ART

In order to provide a sulfated polysaccharide having an biological activity., various methods for desulfating a sulfated polysaccharide have been studied. As a method for desulfating a sulfated polysaccharide, there has been known a method of carrying out desulfation by an acid catalyst in hydrogen chloride/methanol (Kantor T. G. and Schubert M., J. Amer. Chem. Soc. Vol. 79, p. 152 (1957)). However, in this method, it is impossible to desulfate only a specific sulfate group(s), and cleavage of a sugar chain due to methanolysis of a glycoside bond occurs to lower the molecular weight, whereby the yield of a reaction product having an original chain length is lowered.

As a method for carrying out desulfation with good yield, there may be mentioned solvolysis carried out in an aprotic solvent such as dimethylsulfoxide (DMSO), N,N-dimethylformamide (DMF) or pyridine, etc. (Usov A. et al. Carbohydr. Res., Vol. 18, p. 336 (1971)) or in DMSO containing a small amount of water or methanol (Nagasawa K. et al. Carbohydr. Res., Vol. 58, p. 47 (1977), Nagasawa K. et al. J. Biochem., Vol. 86, p. 1323 (1979)). It has been known that the reaction mechanism of solvolysis is a reverse reaction of a sulfation reaction carried out by using a complex of sulfur trioxide and an amine in an aprotic solvent. This reaction can be used as a method for selective desulfation of an N-sulfate group(s) by controlling reaction conditions. However, an O-sulfate group(s) bonded to a primary or secondary hydroxyl group(s) cannot be eliminated. Further, when this method is applied to an oligosaccharide or a polysaccharide, there are problems that an operation of removing the solvent such as DMSO, etc. after the reaction is complicated, it is necessary to raise the reaction temperature in order to carry out complete desulfation, cleavage of a glycoside bond occurs under such reaction conditions, etc.

On the other hand, as a method for specifically desulfating a sulfate group(s) bonded to a primary hydroxyl group(s) of a saccharide, there may be mentioned a method of using N,O-bis(trimethylsilyl)acetamide (BTSA) (Matsuo, M. et al., Carbohydr. Res., Vol. 241, pp. 209–215 (1993)). When this method is applied to heparin, a sulfate group at 6-position of glucosamine is removed relatively specifically. However, as a result of examining a detailed structure thereof by an enzymatic digestion method, it has been found that simultaneously with eliminating a sulfate group(s) bonded to a primary hydroxyl group(s), elimination of a small amount of an N-sulfate group(s) occurs. Therefore, a method for removing a sulfate group(s) bonded to a primary hydroxyl group(s) with higher selectivity has been demanded. Development of a method for specific elimination of a sulfate group(s) bonded to a primary hydroxyl group(s) is very important for providing a sulfated polysaccharide for the purpose of creating a medicine having a preferred biological activity to human. For example, dextran sulfate, xylan sulfate, chondroitin sulfate, heparin, etc. which are sulfated polysaccharides have been used as a lipometabolism-improving agent or an anti-thrombus agent. However, it has been also known that in one in which sulfate groups are introduced artificially, the positions of introduced sulfate groups cannot be specified, and accompanied with introducing a large amount of sulfate groups, a side effect that a tendency of hemorrhage from tissues is strengthened is caused. Also, sulfated polysaccharides derived from natural substances are different in the positions and amount of sulfate groups, respectively, depending on difference in origin, and the physiological activities of the respective sulfated polysaccharides are also different slightly.

Desulfation of heparin having ability of specifically bonding to various physiological active proteins is considered to be extremely important. For example, in the structure of heparin which interacts with a basic fibro-blast growth factor (bFGF) to accelerate its stabilization and activity to cellular proliferation, N-sulfate groups and sulfate groups at 2-position of iduronic acid are contained abundantly, and no sulfate group at 6-position is required (Ishihara, M. et al., Glycobiology, Vol. 4, pp. 451–458 (1994)). On the other hand, in order to accelerate an activity to an acidic fibroblast growth factor (aFGF) or FGF-4 (Kaposi's sarcoma FGF), abundant sulfate group at 6-position is also required (Ishihara, M., Glycobiology, Vol. 4, pp. 817–824 (1994)). Therefore, in a heparin selectively desulfated at 6-position, obtained by removing a sulfate group(s) of a primary hydroxyl group(s) (hydroxyl group at 6-position) of glucosamine from heparin, an anticoagulant activity is lowered as compared with heparin before desulfation is carried out. However, an effect of specifically accelerating a bFGF activity is maintained and also an effect of suppressing undesired physiological activities generated from interactions with a large number of other physiological active molecules in vivo at a low level can be expected.

As a composition using a fibroblast growth factor (FGF) and polysaccharides, there have been proposed, for example, a medical composition comprising FGF, a sulfated polysaccharide having an antiviral activity and an excipient described in Japanese Provisional Patent Publication No. 80583/1994, a composition comprising FGF, 2-0-sulfated L-iduronic acid and N-sulfo-D-glucosamine and also containing at least one of oligosaccharides having ability of bonding to FGF constituted by 8–18 saccharides described in European Patent Publication No. 509517, and a complex of FGF mutein and glycosaminoglycan or a composition into which these are formulated described in Japanese Provisional Patent Publication No. 40399/1990. Among them, as the sulfated polysaccharide used in the medical composition described in U.S. Pat. No. 5,288,704, desulfated one is not described, and the medical composition is aimed at enhancement of an antiviral activity by a cooperative action. Also, the composition described in European Patent Publication No. 509517 uses a specific oligosaccharide which is not desulfated, and the composition described in Japanese Provisional Patent Publication No. 40399/1990 uses natural glycosaminoglycan which is not subjected to desulfation treatment.

For the purpose of making an inherent biological activity of the sulfated polysaccharide being expressed more specifically with less side effects such as a hemorrhagic action, etc. by desulfating only a sulfate group(s) bonded to a primary hydroxyl group(s) of a sulfated polysaccharide, the present inventor has studied intensively a desulfation process in which positional selectivity is high and side reactions such as cleavage of a glycoside bond, elimination of an N-sulfate group(s), etc. are not caused, to accomplish the present invention.

DISCLOSURE OF THE INVENTION

The present invention is a process for producing a desulfated polysaccharide, which comprises reacting a sulfated polysaccharide having a saccharide in which a primary hydroxyl group is sulfated, as a constituent sugar, with a silylating agent represented by the following formula (I)

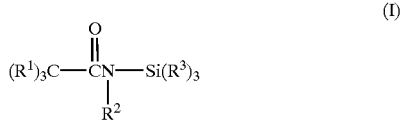

(I)

wherein $R^1$s are the same or different and each represent a hydrogen atom or a halogen atom, $R^2$ represents a lower alkyl group, and $R^3$s are the same or different and each represent a lower alkyl group, an aryl group or a halogen atom, to selectively desulfate a sulfate group bonded to the primary hydroxyl group.

In the above process, it is preferred that the sulfated polysaccharide is converted into an organic solvent-soluble salt such as an organic basic salt, etc., and the reaction is carried out in an organic solvent.

Also, it is preferred that after the desulfation reaction, a silyl group(s) of a silylated hydroxyl group(s) is/are removed.

The present invention also provides a selectively desulfated heparin which comprises having the following characteristics:

(1) in an unsaturated disaccharide composition measured by a method using enzymatic digestion and high performance liquid chromatography, the ΔDiHS-tri(U,6,N)S content shown in FIG. 2 is 10 to 40%, and the ΔDiHS-di(U,N)S content of the same is 30 to 60%, (2) the content of a disaccharide containing an N-substituted sulfate group(s) is 75 to 95%, (3) the weight average molecular weight (Mw) is 4,000 to 30,00dalton, (4) the anti-thrombin activity is 20 U/mg to 150 U/mg, and (5) the effect of accelerating the activity of a basic fibroblast growth factor to cellular proliferation is maintained to be 80% or more of that of heparin which is not desulfated.

Further, the present invention provides a selectively desulfated heparin obtained by desulfating heparin according to the above production process, and having the above characteristics (1) to (5).

Further, the present invention provides an agent for accelerating the activity of a basic fibroblast growth factor, containing the above desulfated heparin as an active ingredient, and a composition in which the activity of a basic fibroblast growth factor to cellular proliferation is accelerated, containing the above desulfated heparin and a basic fibroblast growth factor.

BEST MODE FOR PRACTICING THE INVENTION

Figure 1:
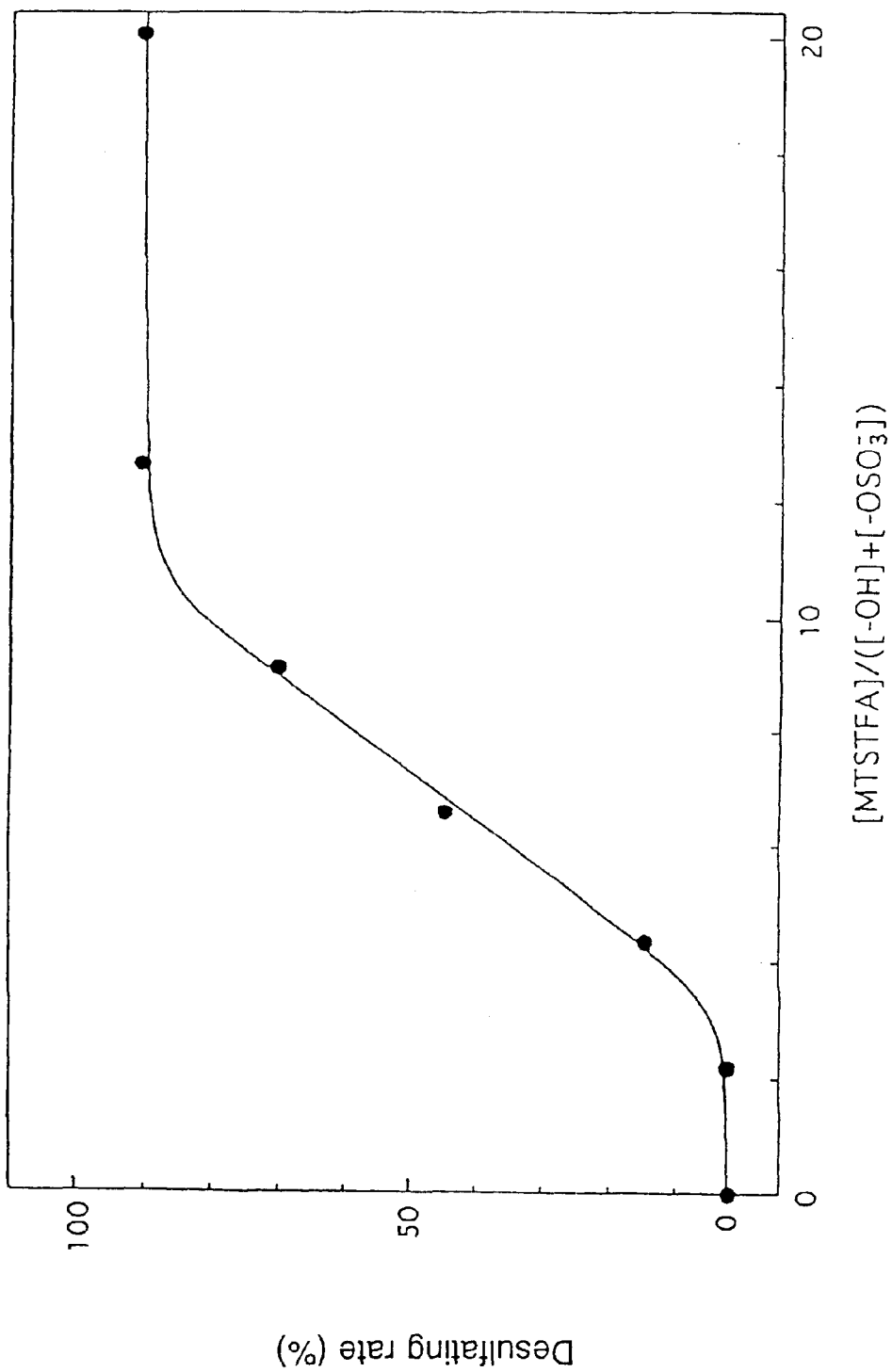
FIG. 1 is a graph showing the desulfation rate of methyl-α-galactopyranoside-6-sulfate, accompanied with change in a MTSTFA amount.

According to the production process of the present invention, complete desulfation or partial desulfation by controlling reaction conditions, of a sulfate group(s) bonded to a primary hydroxyl group(s) (when the constituent sugar unit comprises pentose or hexoses, said group represents a hydroxyl group at 5-position or 6-position, respectively) of a sulfated polysaccharide can be carried out with positional selectivity.

The sulfated polysaccharide to which the process of the present invention is applied is not particularly limited so long as it is a polysaccharide (in the present invention, "polysaccharide" is used as a term including an oligosaccharide and a complex polysaccharide) having a saccharide in which primary hydroxyl groups are sulfated, as a constituent sugar. Such a sulfated polysaccharide may be one which is isolated by extraction from a natural substance or synthesized. As such a sulfated polysaccharide, there may be mentioned one having N-substituted glycosamine as a constituent sugar, and particularly preferred is one having N-sulfated glycosamine having an N-sulfate group(s) which is easily desulfated by a conventional desulfation process, as a constituent sugar.

As the sulfated polysaccharide to be used in the present invention, there may be specifically mentioned one having N-substituted glycosamine in which a primary hydroxyl group is sulfated, as a constituent sugar, etc. The N-substituted glycosamine may be exemplified by glycosaminoglycan having N-sulfated or N-acetylated glucosamine or galactosamine as a constituent sugar, for example, heparin, heparan sulfate, chondroitin sulfate, dermatan sulfate, keratan sulfate, etc.; funoran having D-galactose-6-sulfate as a constituent sugar; and porphyran having L-galactose-6-sulfate as a constituent sugar, etc.

In the present invention, the desulfation reaction is carried out generally in an organic solvent so that the sulfated polysaccharide is provided for the reaction as a salt which is soluble in an organic solvent. As such an organic solvent-soluble salt, there may be mentioned an organic basic salt of the sulfated polysaccharide, and as an organic base, there may be mentioned an aromatic amine such as pyridine, dimethylaniline, diethylaniline, etc.; a tertiary amine such as trimethylamine, triethylamine, tributylamine, N,N-diisopropylethylamine, trioctylamine, N,N,N',N'-tetramethyl-1,8-naphthalenediamine, etc.; an N-alkyl heterocyclic amine such as N-methylpyrimidine, N-ethylpyrimidine, N-methylmorpholine, N-ethylmorpholine, etc., and others. The organic basic salt of the sulfated polysaccharide can be obtained easily by reacting a free sulfated polysaccharide with an organic base.

The desulfation reaction is achieved by making the silylating agent represented by the above formula (I) act on the sulfated polysaccharide generally in an anhydrous organic solvent. By this reaction, a sulfate group is eliminated from a sulfated hydroxyl group, and silylation of the hydroxyl group is also caused.

As the organic solvent to be used in the reaction, the above organic bases (pyridine, etc.) used for formation of the salt of the sulfated polysaccharide are preferred, but in place of the organic base, there may be used an aprotic solvent such as acetonitrile, N,N-dimethylformamide (DMF), dimethylsulfoxide (DMSO), N,N-dimethylacetamide, tetrahydrofuran (THF), 1,4-dioxane, etc.

In the compound represented by the formula (I), which is a silylating agent, $R^1$s are the same or different and each represent a hydrogen atom or a halogen atom such as fluorine, etc., $R^2$ represents a lower alkyl group having 1 to 6 carbon atoms such as methyl, ethyl, propyl, isopropyl, butyl, isobutyl, sec-butyl, tert-butyl, pentyl, isopentyl, hexyl, etc., and $R^3$s are the same or different and each represent the same lower alkyl group as described above, an aryl group such as phenyl, etc., or a halogen atom such as chlorine, fluorine, etc. $(R^3)_3Si$ in the formula (I) may be exemplified by trimethylsilyl, triethylsilyl, dimethylisopropylsilyl; isopropyldimethylsilyl, methyldi-t-butylsilyl, t-butyldimethylsilyl, t-butyldiphenylsilyl and triisopropylsilyl groups, etc. Most preferred as the silylating agent represented by the formula (I) is N-methyl-N-trimethylsilylacetamide (MTMSA) or N-methyl-N-trimethylsilyl-trifluoroacetamide (MTSTFA).

The reaction is completed at room temperature to 100° C. within several minutes to several ten hours. At a temperature which is lower than room temperature, the reaction does not proceed sufficiently, while at a temperature of 100° C. or higher, the glycoside bond of the sulfated poly-saccharide might be cleaved. By changing the reaction conditions, particularly the reaction temperature, the degree of desulfation can be controlled. For example, by the reaction at 30 to 100° C for about 30 minutes to 3 hours, preferably at 65 to 90° C. for 30 minutes to 2 hours, partial desulfation of the existing sulfate groups can be carried out, and by the reaction at 90 to 100° C. for about 2 to 6 hours, more complete desulfation can be carried out.

The amount of the silylating agent to be used is about 3—to 100—fold moles, preferably about 3—to 30—fold moles based on one mole of all hydroxyl groups (all of unsubstituted and substituted hydroxyl groups) of the sulfated polysaccharide. Also, by changing the amount of the silylating agent to be used, the degree of desulfation can be controlled.

Thus, a desulfated polysaccharide in which sulfate groups bonded to primary hydroxyl groups of the sulfated polysaccharide are removed partially or completely can be obtained. After the desulfation reaction, in order to make an unreacted silylating agent non-reactive, or in order to remove silyl groups bonded to hydroxyl groups of the desulfated polysaccharide, an object can be achieved by, for example, adding water to the reaction mixture and/or dialyzing the reaction mixture to water. Further, if necessary, a reaction for removing silyl groups can be also carried out according to a conventional method. This reaction is carried out by, for example, making the solution subjected to the above treatment exist under an alkaline condition of about pH 9 to 9.5 or under a heating condition.

When an anionic functional group exists in the desulfated polysaccharide, a salt can be formed by making a counter ion corresponding thereto exist in the solution. For example, an alkali metal salt of the desulfated polysaccharide can be obtained by adding an alkali metal hydroxide (sodium hydroxide, etc.) to an aqueous solution of the desulfated polysaccharide after the reaction for removing silyl groups, dialyzing the mixture, if necessary, and then subjecting the mixture to a dehydration step under a non-heating condition such as lyophilization, etc. Specifically, in order to convert sulfate groups remaining in these into Na salts, sodium hydroxide is added to adjust pH of the solution to about 9, and the mixture is dialyzed and then lyophilized to obtain a sodium salt of the desulfated polysaccharide.

Among the desulfated polysaccharides which are desulfated selectively, obtainable by the production process of the present invention, heparin is particularly preferred, and this selectively desulfated heparin has the following characteristics.

(1) In an unsaturated disaccharide composition measured by a method using enzymatic digestion and high performance liquid chromatography, the ΔDiHS-tri(U,6,N)S content is 10 to 40%, and the ΔDiHS-di(U,N)S content is 30 to 60%, (2) the content of a disaccharide containing an N-substituted sulfate group(s) is 75 to 95%, (3) the weight average molecular weight Mw is 4,000 to 30,000 dalton, (4) the anti-thrombin activity shows a value of 20 U/mg to 150 U/mg, and (5) the effect of accelerating the activity of a basic fibroblast growth factor to cellular proliferation is maintained to be 80% or more of that of heparin which is not desulfated.

Figure 2:
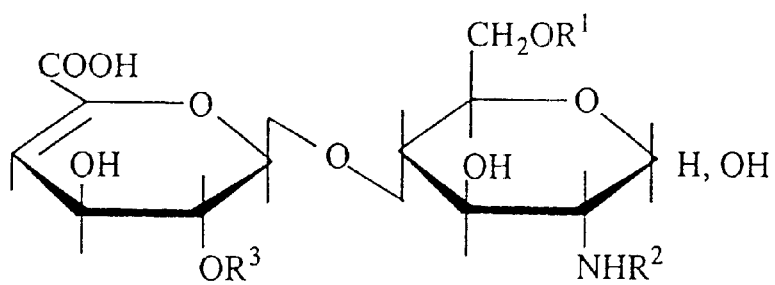
FIG. 2 shows a relation between the structures and abbreviated names of various unsaturated disaccharide isomers generated by enzymatically digesting glycosaminoglycan. In the figure, Ac represents an acetyl group.

Here, the ΔDiHS-tri(U,6,N)S content of (1) is a value obtained by a test method "Analysis of disaccharide by enzymatic digestion" described below, and means a content of one in which 2-position of uronic acid and an amino group and 6-position of glucosamine are sulfated, among various unsaturated disaccharides (see FIG. 2) generated as a result of decomposing the heparin by heparin-decomposing enzymes. Similarly, the ΔDiHS-di(U,N)S content means a content of one in which 2-position of uronic acid and an amino group of glucosamine are sulfated. It is preferred that the ΔDiHS-tri(U,6,N)S content is 10 to 20%, and the ΔDiHS-di(U,N)S content is 50 to 60%.

The content of a disaccharide containing N-substituted sulfate groups of (2) is a content (mole %) of a disaccharide containing N-substituted sulfate groups based on all constituent sugar units in the heparin subjected to desulfation.

The weight average molecular weight of (3) is a value of a weight average molecular weight (Mw) determined by high performance gel permeation chromatography with a molecular weight standard product of chondroitin sulfate being a control, and it is preferably 10,000 to 20,000 dalton.

In the case of measurement by gel permeation chromatography, the weight average molecular weight of heparin before it is desulfated is generally in the range of 4,000 to 30,000 dalton, and the weight average molecular weight of the heparin desulfated by the process of the present invention is almost unchanged.

In Examples, the molecular weights before and after desulfation were measured under the following conditions.

Gel permeation (GPC) HPLC
  Column: TSK gel G-4000+G-3000+G-2500 (manufactured by Tosoh K. K.)
  Solvent: 0.2 M NaCl, 1.0 ml/min
  Detector: differential refractometer (RI), UV absorption (UV 230 nm)
  Charging amount: 5 µl (10 mg/ml)

The anti-thrombin activity of (4) is a value measured by a method described in Examples described below. When the anti-thrombin activity of heparin which is not desulfated is measured by said method, its value shows 1,200 U/mg to 1,600 U/mg, but the anti-thrombin activity of the desulfated heparin of the present invention is in the range of 20 U/mg to 150 U/mg, preferably 30 U/mg to 100 U/mg, and an hemorrhagic action is reduced.

The effect of accelerating the activity of a basic fibroblast growth factor to cellular proliferation of (5) is a bFGF activity-maintaining effect of the desulfated heparin of the present invention relative to a bFGF activity-maintaining effect by heparin before treatment with a desulfating agent when cellular proliferation is measured by a test method "Measurement of bFGF and aFGF activities-accelerating effect" described below, which is shown by percentage. Even after desulfation, the desulfated heparin of the present invention maintains 80 to about 100% of the activity-accelerating effect possessed by heparin which is not desulfated.

The selectively desulfated heparin obtained by the production process of the present invention provides an agent for accelerating the activity of a basic fibroblast growth factor, containing the same as an active ingredient, and can also provide a composition in which the activity of a basic fibroblast growth factor to cellular proliferation is accelerated, by mixing the same with a basic fibroblast growth factor.

By administering the desulfated heparin of the present invention internally or externally of vital bodies, the activity of bFGF is stabilized, which is useful for treating or preventing, for example, wound healing (decubitus, etc.), etc. In diabetics, heparan sulfate or heparin might be reduced, and it is considered that the activity of bFGF used for wound healing does not exhibit sufficiently without heparan sulfate or heparin so that the above composition of the present invention is particularly useful for treating and preventing decubitus of diabetics. Also, when patients and administration sites in which endogenous bFGF is produced sufficiently are treated, it is not necessarily required to administer bFGF from outside, and an object can be achieved sufficiently only by the desulfated heparin of the present invention so that the above bFGF activity-accelerating agent can be used for the purpose of wound healing, etc. As a preparation form and an administration route when the bFGF activity-accelerating agent or the above composition of the present invention is administered internally or externally of viral bodies, they can be safely administered parenterally or orally to warm-blooded animals (e.g., human, mice, rats, hamsters, rabbits, dogs, cats, etc.) as such or as a medical composition (e.g., an injection, a tablet, a capsule, a solution, an ointment, etc.) with other pharmaceutically acceptable carrier, excipient, diluent, etc.

Also, in the bFGF activity-accelerating agent and the above composition of the present invention, side effects such as a hemorrhagic action, etc. are reduced so that safety as a medicine is high.

EXAMPLES

In the following, the present invention is explained in more detail by referring to Example and Test example, but these do not limit the scope of the present invention.

Identification of a sulfated polysaccharide was carried out based on the following methods.

Test methods

1) Analysis of disaccharide by enzymatic digestion

Analysis of the positions of sulfate groups after desulfation of glycosaminoglycan can be carried out as described below. That is, glycosaminoglycans before and after treatment of a desulfation reaction were digested with enzymes, and the produced unsaturated disaccharides were analyzed by high performance liquid chromatography (HPLC) (see "2•8 Structure analysis using glycosaminoglycan-decomposing enzymes and HPLC in combination" described in New Bio-chemical Experiment Lecture 3, Carbohydrates II (1991) pp. 49–62).

Digestion with heparin-decomposing enzymes

According to the method of New Biochemical Experiment Lecture 3, Carbohydrates II pp. 54–59 (published by Tokyo Kagaku Dojin, 1991), 0.1 mg of heparin was dissolved in 220 $\mu$l of 20 mM sodium acetate (pH 7.0) containing 2 mM calcium acetate, and 20 mU of heparinase and 20 mU of heparitinases I and II were added to the solution. The mixture was reacted at 37° C. for 2 hours. In the case where sulfate groups bonded to amino groups was eliminated by desulfation treatment, heparin-decomposing enzymes do not act on such a desulfated heparin so that it is necessary to acetylate amino groups previously prior to an enzymatic reaction. N-acetylation proceeds quantitatively with acetic anhydride in an aqueous solution containing sodium carbonate or a Dowex (Dowex-1 ($HCO_3$) type) ion exchange resin (see "Sugar Chain Engineering", published by K. K. Sangyo Chosakai and Biotechnology Information Center, p. 324).

Analysis by HPLC

50 $\mu$l of the solution after digestion with the heparin-decomposing enzymes was carried out, was analyzed by using HPLC (Irika, Model 852). Absorbance at 232 nm was measured by using an ion exchange column (Dionex Co., CarboPac PA-1 column, 4.0 mm×250 mm). The measurement was carried out according to a method of using a gradient system (50 mM→2.5 M) using lithium chloride at a flow rate of 1 ml/min (Kariya, et al. Comp. Biochem. Physiol. Vol. 103B, pp. 473–479 (1992)).

2) Gel permeation

10 $\mu$l of a 3% sulfated polysaccharide solution was analyzed by gel permeation using HPLC. By using TSK gel-(G4000+G3000+G2500)$PW_{XL}$(Tosoh, 7.8 mm×30 cm) as a column and using 0.2 M sodium chloride as an eluting solution, development was carried out at a flow rate of 1.0 ml/min. For detection of a sulfated polysaccharide, a differential refractometer (Shimadzu, AID-2A) was used.

3) Measurement of bFGF and aFGF activities-accelerating effect

A31 cells (BALB/c 3T3) passage of which was maintained in a DMEM medium (produced by Life Technologies Co.) containing 10% bovine serum were plated on a 96-multiwell culture plate with 100 $\mu$l of $ITS^+$(produced by Collaborative Research Co.) containing 1 $\mu$l/ml of a test sample, 20 mm $NaClO_3$ and $SO_4^{2-}$ free DMEM containing 2 ng/ml of human recombinant bFGF (hrbFGF) (produced by Seikagaku Kogyo K. K.) or 5 ng/ml of human recombinant bFGF (hrbFGF) (produced by Seikagaku Kogyo K. K.). After culturing for 3 days, 20 $\mu$l of a cell titer 96AQ non-radioactive cellular proliferation assay solution (produced by Seikagaku Kogyo K. K.) was added to the respective wells. After culturing at 37° C. for 2 hours, $OD_{490}$ was measured to quantitate cellular proliferations of the respective wells. In Table 2, in both of bFGF and aFGF, cellular proliferation when 1 $\mu$l/ml of heparin which was not desulfated was added was defined as 100, and that when said heparin was not added was defined as 0.

4) Measurement of anti-thrombin activity

Three solutions of 350 $\mu$l of a 20 mM Tris buffer (pH 7.4) containing 150 mM salt, 10 mM calcium chloride and 0.1% bovine serum albumin, 100 $\mu$l of a bovine anti-thrombin III solution (1 U/ml of the same buffer) and 100 $\mu$l of the multiple-diluted heparin sample were mixed in a cooled state, and the mixture was incubated at 37° C. for 2 minutes. 50 $\mu$l of a bovine thrombin solution (50 mU/ml in distilled water) was added to this solution, and the mixture was incubated at 37° C. for 5 minutes. Then, 100 $\mu$l of a substrate solution (Boc-Val-Pro-Arg-MCA, a 70 $\mu$M aqueous solution) was added thereto, and the mixture was stirred. The mixture was incubated at 37° C. for 3 minutes, and 300 μl of 30% acetic acid was added thereto to terminate the reaction. The fluorescent intensity of the reaction mixture was measured at an excitation wavelength of 350 nm and a fluorescent wavelength of 444 nm. A blank 1 measured by using distilled water in place of the sample of the above reaction mixture composition and a blank 2 of the reaction mixture containing only the substrate and the buffer were treated in the same manner, and the fluorescent degrees were determined.

A thrombin activity-inhibiting rate was determined by the following equation, and the respective inhibition rates at the sample concentrations were plotted on a semilogarithmic graph to determine 50% inhibition rates ($IC_{50}$). The results are shown in Table 2.

Thrombin activity-inhibiting rate $$(\%) = 100 - (\Delta Fs/\Delta Fb) \times 100$$

wherein ΔFs: fluorescent intensity of sample—fluorescent intensity of blank 1

ΔFb: fluorescent intensity of blank 2 —fluorescent intensity of blank 1

Test example 5 ml of an Amberlite IR-120($H^{3o}$) type resin was added to an aqueous solution of about 2 mg/3 ml of methyl-α-galacto-pyranoside-6-sulfate ammonium salt to convert the salt into a free sulfate ester type. After the resin was removed, 2 ml of pyridine was added to the residue to form a pyridinium salt. Residual pyridine was removed by evaporation under reduced pressure, and the residue was lyophilized to prepare dry methyl-a-galactopyranoside-6-sulfate pyridinium salt. This sample was subdivided into 0.2 mg, respectively, and about 0.05 ml of dry pyridine and methyl-a-glycoside as an internal standard were added thereto to prepare different reaction systems in which the molar amount of MTSTFA based on the molar amount of all hydroxyl groups ($[-OH]+[-O-SO_3^-]$) of methyl-α-galactopyranoside-6-sulfate pyridinium salt was 0 to 20 times. After MTSTFA was added to the respective systems, the mixtures were reacted by heating at 80° C. for about 2 hours. In order to carry out gas chromatography analysis after complete 0-trimethylsilylation, trimethylsilylimidazole was added to the reaction mixtures, and the mixtures were heated at 80° C. for 20 minutes. By measuring trimethylsilylated methyl-α-galactopyranoside in the reaction mixtures of the respective systems directly by gas chromatography, desulfation amounts were calculated, which are shown in FIG. 1. From FIG. 1, it can be seen that in the case of the sulfated monosaccharide, when MTSTFA is used in an about 13-fold molar amount or more based on the molar amount of all hydroxyl groups of the saccharide under the above reaction conditions, sulfate esters of primary hydroxyl groups can be desulfated almost completely.

EXAMPLE 200 mg of sodium salt (weight average molecular weight: 12,200 dalton) of heparin was applied to an Amberlite IR-120 ($H^+$type) column (1×10 cm), and by adding excess pyridine to an eluting solution, the solution was neutralized to have pH 8 and lyophilized to prepare a pyridinium salt of heparin. This pyridinium salt of heparin was dissolved in 20 ml of dehydrated pyridine to prepare a reaction sample. MTSTFA in a 20-fold molar amount (about 4 ml) of the sugar skeleton of heparin was added to the sample, and the mixture was stirred at 65, 75, 85, 90 and 95° C. for 2 hours. After completion of the reaction, 20 ml of water was added to make unreacted MTSTFA non-active, whereby the reaction was terminated. The reaction mixture was dialyzed by using a Millipore ultrafiltration membrane to obtain a solution of a product obtained by desulfation treatment of the trimethylsilylated heparin.

Next, in order to remove trimethylsilyl groups by hydrolysis, the dialyzed solution was boiled by heating at 100° C. for 30 minutes to 1 hour (until the solution became transparent). After sodium hydroxide was added to adjust the solution to pH 9 to 9.5, the solution was dialyzed. The dialyzed solution was lyophilized to obtain a sodium salt corresponding to 130 mg of the product obtained by desulfation treatment of the heparin.

Comparative example

As a control experiment, according to Example, a reaction was carried out at 90° C. by using N,O-bis(trimethylsilyl)-acetamide (BTSA) in place of MTSTFA.

The analyzed disaccharide values by enzymatic digestion before and after the above treatment of the heparin with the silylating agent are shown in Table 1.

The above respective products obtained by desulfation treatment of the heparin were reacted at 4° C. for 2 hours in a sodium carbonate aqueous solution (pH 6.5) by using acetic anhydride and methanol to be acetylated. These samples were decomposed by using hepaxin-decomposing enzymes according to the analytic method described in the above Test methods, various isomers (FIG. 2) of a produced unsaturated disaccharide were fractionated by HPLC, and the results of analyzing compositional ratios thereof are shown in Table 1.

TABLE 1

Disaccharide comparison of heparin

| Sample | Temperature | ΔDiHS- OS | NS | 6S | US | di(6,N)S | di(U,N)S | di(U,6)S | tri(U,6,N)S | Total | Yield of disaccharide (%) | 6-Position desulfation rate (%) |
|---|---|---|---|---|---|---|---|---|---|---|---|---|
| Before treatment | | 4.3 | 3.8 | 0.7 | 1.3 | 8.1 | 24.8 | 0 | 52.6 | 95.6 | 91 | 0 |
| BTSA treatment (Comparison) | 90° C. | 7.6 | 4.3 | 1.4 | 11.2 | 6.0 | 47.4 | 4.0 | 10.5 | 92.4 | 75 | 64.3 |
| MTSTFA treatment (present invention) | 65° C. | 5.5 | 2.9 | 1.1 | 2.8 | 7.9 | 34.7 | 1.7 | 36.7 | 93.3 | 86 | 24.4 |
| | 75° C. | 5.9 | 3.8 | 0.5 | 1.2 | 5.8 | 47.4 | 0.1 | 27.5 | 92.2 | 81 | 44.8 |
| MTSTFA treatment (present invention) | 85° C. | 6.9 | 3.8 | 0.9 | 8.0 | 6.1 | 51.7 | 1.3 | 14.9 | 93.6 | 79 | 62.2 |

TABLE 1-continued

Disaccharide comparison of heparin

| Sample | Temperature | ΔDiHS- | | | | | | | | Total | Yield of disaccharide (%) | 6-Position desulfation rate (%) |
| --- | --- | --- | --- | --- | --- | --- | --- | --- | --- | --- | --- | --- |
| | | OS | NS | 6S | US | di(6,N)S | di(U,N)S | di(U,6)S | tri(U,6,N)S | | | |
| MTSTFA treatment (present invention) | 90° C. | 6.2 | 5.3 | 0.3 | 4.2 | 6.8 | 59.3 | 0.6 | 12.7 | 95.4 | 78 | 66.8 |
| MTSTFA treatment (present invention) | 95° C. | 6.3 | 9.4 | 0 | 2.4 | 5.3 | 67.6 | 0 | 1.6 | 92.6 | 65 | 88.8 |

ΔDiHS- represents an unsaturated disaccharide generated by enzymatic digestion. The yield of a disaccharide was calculated from an area value of gel permeation HPLC.

Table 1 shows that by both BTSA and MTSTFA treatments, ΔDiHS-Tri(U,6,N) derived from the disaccharide as a main constituent component of the heparin was significantly lowered and ΔDiHS-di(U,N)S was increased by elimination of sulfate groups at 6-position. However, in BTSA treatment, elimination of N-sulfate groups further occurred to cause reduction of the total amount of ΔDiHS-di(U,N)S and ΔDiHS-Tri(U,6,N)S and increase in ΔDiHS-US. That is, it can be seen that in MTSTFA treatment, a sulfate group of a primary hydroxyl group of the heparin could be removed to the same extent as in BTSA treatment, and further, by suppressing reduction of an N-sulfate group by BTSA treatment, it acted on a sulfate group at 6-position more selectively.

Further, as a result of examining change in the molecular weights by gel permeation with respect to the heparins before and after MTSTFA treatment, almost no change in the molecular weights was observed.

From the foregoing, it is clear that the desulfation reaction by MTSTFA acts specifically on a sulfate group bonded to a primary hydroxyl group and does not exert influence on sulfate groups at other positions nor a glycoside bond.

Also, the thrombin-inhibiting activity and the bFGF and aFGF activities-accelerating effect of the heparin the sulfate group at 6-position of which was desulfated at 65° C., 75° C., 85° C., 90° C. and 95° C. stepwisely were examined. The results are shown in Table 2.

TABLE 2

| Heparin de-sulfated at 6-position | Inhibition of thrombin activity (IC$_{50}$ ng/ml) (U/mg) | Acceleration of bFGF activity | Acceleration of aFGF activity |
| --- | --- | --- | --- |
| Native | 8.75 (1430 U/ml) | 100 | 100 |
| 65° C. | 1.31 × 10$^2$ (96 U/ml) | 88 | 72 |
| 75° C. | 1.42 × 10$^2$ (88 U/ml) | 89 | 41 |
| 85° C. | 1.67 × 10$^2$ (75 U/ml) | 91 | 18 |
| 90° C. | 2.98 × 10$^2$ (43 U/ml) | 87 | 11 |
| 95° C. | 8.84 × 10$^3$ (1.4 U/ml) | 26 | 12 |

As shown in Table 2, whereas the thrombin-inhibiting rate shows abrupt reduction in partial desulfation at 6-position at 65° C., the bFGF activity-accelerating effect is maintained until desulfation at 90° C. On the other hand, the aFGF activity-accelerating effect showed mild reduction with desulfation of the sulfate group at 6-position. Particularly, by carrying out desulfation of the sulfate group at 6-position at a reaction temperature of 85 to 90° C., a heparin selectively desulfated at 6-position, in which an anticoagulant activity, an aFGFG activity-accelerating effect, etc. were suppressed and a specific bFGF activity-accelerating effect was maintained, was obtained.

When heparin having a weight average molecular weight in the range of 4,000 to 30,000 was desulfated by the process of the present invention in the same manner as described above, 6-position is desulfated specifically in the same manner as shown in Table 1, the biological activities show the same tendency as shown in Table 2, and there is almost no change in the molecular weight before and after desulfation treatment.

Utilizability in industry

According to the present invention, among sulfate groups having different properties bonded to the sugar skeleton of a sulfated polysaccharide, only a sulfate group of a primary hydroxyl group is specifically desulfated by recognizing difference between a sulfate group of a primary hydroxyl group, a sulfate group of a secondary hydroxyl group and an N-sulfate group, whereby a sulfated polysaccharide having sulfate esters at specific positions, which has not been known in the prior art, can be produced.

Particularly in a product subjected to desulfation treatment obtained by desulfating heparin by the process of the present invention, a nonspecific bonding of heparin to proteins is suppressed, and a specific physiological activity by an interaction with a basic fibroblast growth factor (bFGF) is obtained. Further, said product can be applied to a wide range of medicines such as a medicine with less side effects such as a hemorrhagic tendency, etc. for treating wounds, burns or dermal ulcer, a medicine for treating osteoporosis, a medicine for treating fracture, a medicine for treating digestive ulcer, a medicine for improving prognosis of cardiac infarction, etc., in combination with bFGF or singly.

Also, a wide range of applications of the desulfation process of the present invention to physiological active molecules other than bFGF can be expected.

What is claimed is:

1. A primary hydroxy group of N-acetylglucosamine selectively desulfated heparin having the following characteristics for an enzyme digestion product of the heparin:

(1) contents of unsaturated disaccharides of the following formulae (a) and (b)

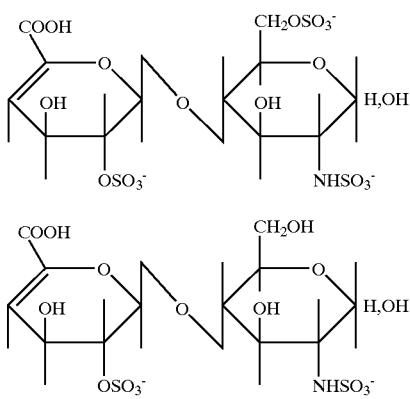

(a)

(b)

measured by high performance liquid chromatography in the enzyme digestion product of the selectively desulfated heparin are less than 40% and 30 to 67.6%, respectively, and (2) a content of disaccharides containing an N-substituted sulfate group is 75 to 95%, (3) the weight average molecular weight Mw is 4,000 to 30,000 dalton.

2. A method for treating wounds or ulcers in warm-blooded animals comprising administering to warm-blooded animals in need thereof an amount of the product of claim 1 sufficient to treat wounds or ulcers.

3. A primary hydroxy group of N-acetylglucosamine selectively desulfated heparin of claim 1 further having the following characteristics:

(1) contents of unsaturated disaccharides of the following formulae (c) and (d)

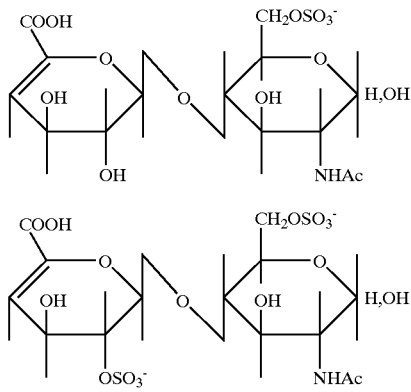

(c)

(d)

measured by high performance liquid chromatography in the enzyme digestion product of the selectively desulfated heparin are 1.1% or less and 1.7% or less, respectively.

4. A method for treating wounds, burns, dermal ulcer, osteoporosis, fracture or digestive ulcer in warm-blooded animals comprising administering to warm-blooded animals in need thereof an amount of the product of claim 3 sufficient to treat wounds, burns dermal ulcer, osteoporosis, fracture or digestive ulcer.

* * * * *